United States Patent
Ilmoniemi et al.

(10) Patent No.: US 10,780,291 B2
(45) Date of Patent: Sep. 22, 2020

(54) MTMS COIL DEVICE WITH OVERLAPPING COIL WINDINGS

(71) Applicant: Nexstim Oy, Helsinki (FI)

(72) Inventors: Risto Ilmoniemi, Aalto (FI); Lari Koponen, Aalto (FI); Jaakko Nieminen, Aalto (FI); Gustaf Järnefelt, Helsinki (FI)

(73) Assignee: Nexstim Oyj, Helsinki (FI)

( * ) Notice: Subject to any disclaimer, the term of this patent is extended or adjusted under 35 U.S.C. 154(b) by 0 days.

(21) Appl. No.: 14/294,573

(22) Filed: Jun. 3, 2014

(65) Prior Publication Data

US 2014/0357935 A1 Dec. 4, 2014

Related U.S. Application Data

(63) Continuation of application No. PCT/FI2014/050447, filed on Jun. 3, 2014.

(60) Provisional application No. 61/830,181, filed on Jun. 3, 2013.

(51) Int. Cl.
*A61N 2/02* (2006.01)
*A61N 2/00* (2006.01)

(52) U.S. Cl.
CPC .............. *A61N 2/02* (2013.01); *A61N 2/004* (2013.01); *A61N 2/006* (2013.01)

(58) Field of Classification Search
CPC ..... A61N 2/004; A61N 2/006; A61N 2/00–12
See application file for complete search history.

(56) References Cited

U.S. PATENT DOCUMENTS

| | | | |
|---|---|---|---|
| 4,994,015 A | | 2/1991 | Cadwell |
| 5,738,625 A | * | 4/1998 | Gluck ...................... A61N 2/02 128/897 |
| 6,048,302 A | * | 4/2000 | Markoll ................... A61N 2/02 600/13 |
| 6,537,197 B1 | * | 3/2003 | Ruohonen ................ A61N 2/02 335/299 |
| 8,690,748 B1 | * | 4/2014 | Fu ........................ A61N 1/0476 600/15 |

(Continued)

FOREIGN PATENT DOCUMENTS

| CN | 102847231 A | 1/2013 |
|---|---|---|
| JP | 2012125546 A | 7/2012 |

(Continued)

OTHER PUBLICATIONS

"What Are Electromagnetic Fields?" WHO. World Health Organization, Mar. 9, 2010. Web. Jan. 21, 2016. <http://www.who.int/peh-emf/about/WhatisEMF/en/>.*

*Primary Examiner* — Catherine B Kuhlman
(74) *Attorney, Agent, or Firm* — Laine IP Oy

(57) ABSTRACT

Provided herein is a multichannel Transcranial Magnetic Stimulation (mTMS) coil device with two or more overlapping coil windings within a casing. The mTMS coil device is capable of adjusting parameters of the stimulation of magnetic and induced electric fields through the selective control of the multiple coil windings within the mTMS coil device. Additionally, provided are methods of operation including navigated TMS for adjusting parameters such as location, direction and/or orientation of magnetic and induced electric fields from mTMS coil devices.

18 Claims, 15 Drawing Sheets

(56) References Cited

U.S. PATENT DOCUMENTS

| | | |
|---|---|---|
| 2003/0050527 A1* | 3/2003 | Fox .................. A61N 2/02 600/13 |
| 2003/0158583 A1* | 8/2003 | Burnett ............ A61N 1/36071 607/2 |
| 2005/0154426 A1 | 7/2005 | Boveja et al. |
| 2007/0260107 A1* | 11/2007 | Mishelevich ........ A61N 2/004 600/14 |
| 2008/0058581 A1 | 3/2008 | Aho |
| 2009/0156884 A1* | 6/2009 | Schneider .............. A61N 2/02 600/14 |
| 2009/0227829 A1 | 9/2009 | Burnett et al. |
| 2010/0160712 A1* | 6/2010 | Burnett ............ A61N 1/36007 600/13 |
| 2010/0185042 A1* | 7/2010 | Schneider .............. A61N 2/02 600/13 |
| 2010/0331602 A1* | 12/2010 | Mishelevich ........ A61N 2/006 600/13 |
| 2011/0273251 A1* | 11/2011 | Mishelevich ........ A61N 2/006 335/299 |
| 2013/0289433 A1* | 10/2013 | Jin .................. A61N 2/004 600/544 |

FOREIGN PATENT DOCUMENTS

| | | |
|---|---|---|
| WO | WO2008001155 A1 | 1/2008 |
| WO | WO2010080879 A2 | 7/2010 |
| WO | WO2013152355 A1 | 10/2013 |

\* cited by examiner

MTMS COIL DEVICE WITH OVERLAPPING COIL WINDINGS

FIELD OF INVENTION

The present invention relates to multichannel Transcranial Magnetic Stimulation coil devices (mTMS). In particular to mTMS coil device having overlapping coil windings.

BACKGROUND OF INVENTION

Typical TMS coil devices have a single, standard FIG. 8 coil within a casing. The circuitry within or connected to the TMS coil device is able to adjust primarily the amplitude and frequency of stimulation pulses. In order to change the position, direction and/or orientation of a stimulation pulse requires the TMS coil device to be physically moved to the proper position.

Currently, TMS coil devices are typically hand held by an operator. Several tools exist to help the operator place the TMS coil device in the correct location and keep it there. However, several problems persist. One major problem is that the most important parameter for accurate stimulation is the relationship between the TMS coil device and a patient's head. Even if the TMS coil device is kept still and in a good position, if the patient moves their head then the stimulation will no longer be accurate, even without the TMS coil device moving. As it is difficult to keep a patient's head perfectly still the problem of accurate stimulation will always persist if the relationship between the TMS coil device and patient's head remains the key factor for accuracy.

Other problems persist as finding both the proper location and orientation of a TMS coil device in order to provide a desired stimulation can be difficult, awkward and time consuming. Therefore, there exists a need for a way to rely less on the actual position of and orientation of the TMS coil device in relation to a patient's head for accurate stimulation.

Additionally, when multiple coil windings are used in a single casing the number of input and return lines to and from the casing grows and can become unwieldy, making use of the coil device challenging.

SUMMARY OF THE INVENTION

It is an object of the present invention to provide a multichannel Transcranial Magnetic Stimulation (mTMS) coil device.

It is an aspect of certain embodiments to provide an mTMS coil device comprising: a first coil winding having a first power input line, a second coil winding having a second power input line, and wherein the first and second coil windings are at least partially overlapping.

According to certain examples, the mTMS further comprises a casing. The first and second coil windings can be housed within said casing. The first and second coil windings can also only partially overlap within the casing. Furthermore, more than 2, for example 3, 4, 5 or more coil windings can be combined and overlapped in accordance with embodiments of the present invention.

Furthermore, it is an object of the present invention to provide a method of controlling an mTMS coil.

According to certain embodiments the method includes controlling the first power line to generate a first, primary magnetic field. According to certain examples the method further includes modifying the position, direction and/or orientation of the primary magnetic field by separately controlling a second current through the second power line to generate a second, secondary magnetic field. According to certain examples the method further or alternatively includes modifying the position, direction and/or orientation of the primary magnetic field by adjusting the position and/or orientation of the second coil winding with respect to the first coil winding.

Still yet, it is an object of certain embodiments of the present invention to provide a computer readable medium having stored thereon a set of computer readable instructions for causing a processor to carry out the steps of the methods disclosed herein.

DETAILED DESCRIPTION OF EXEMPLARY EMBODIMENTS

Figure 1:
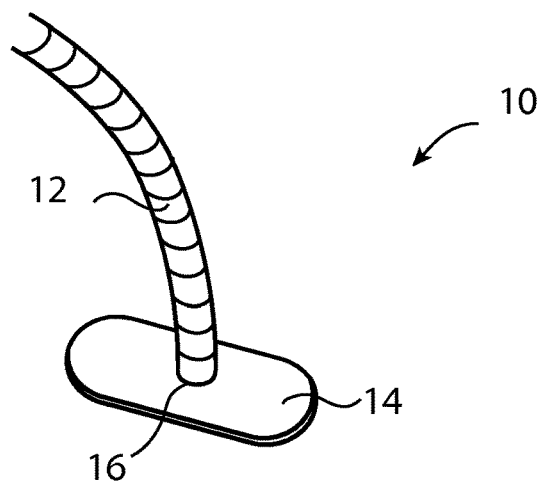
FIG. 1 shows an mTMS coil device.

FIG. 1 shows an example of a multichannel Transcranial Magnetic stimulation (mTMS) coil device 10. The mTMS coil device 10 has a casing 14. The casing 14 has an input cable opening 16 for input/return cabling 12. The mTMS coil device 10 may or may not include the actual input/return cabling 12. Additionally, there may be more than one opening 16 and/or more than one input/return cabling 12.

Figure 2:
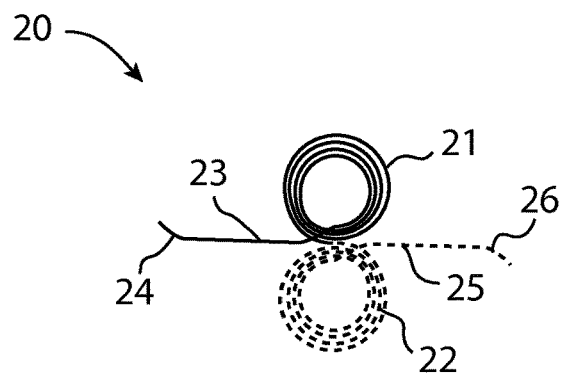
FIG. 2 shows a standard FIG. 8 coil winding.

Within the casing 14 of the mTMS coil device 10 are at least two coil windings. An example of a standard Transcranial Magnetic Stimulation (TMS) coil winding is presented in FIG. 2. Both the solid and dotted lines represent wires which together form the standard coil winding 20. The wires 21 wrapped in a coil which are represented with solid lines have current passing through them in a direction opposite to that of the direction of the wires 22 wrapped in a coil which are represented with a dotted line. By opposite, it is meant either clockwise or counterclockwise direction of current flow. The same convention of solid and dotted lines is continued through the application unless otherwise noted.

The standard coil winding 20 has an input line 24 and a return line 26. The input line 24 is for introducing a current to the coil winding 20. The return line 26 is for returning current, e.g. to a power storage medium, e.g. a capacitor or capacitor bank. In some implementations, the return line 26 may be used for returning current to a dissipation medium, e.g., a power resistor or transistor. In other implementations, some portion of the current may be returned to a capacitor bank while the rest of it is passed to a dissipation element. The input line 24 is typically, but not always, connected to a crossing wire 23. Similarly, the return line 26 is typically connected to a crossing wire 25. Crossing wires will be discussed in more detail below.

Figure 3:
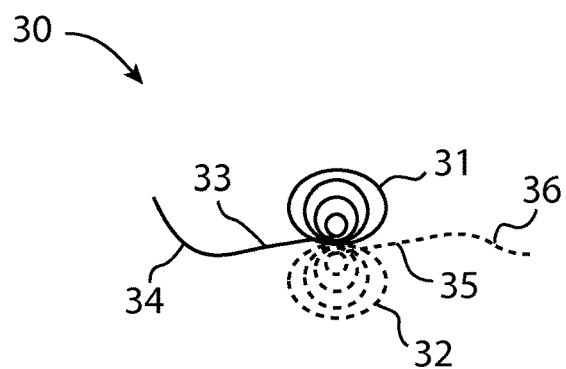
FIG. 3 shows an efficient FIG. 8 coil winding example.

Additionally presented herein is an efficient coil winding 30, as shown for example in FIG. 3. The efficient coil winding 30 has generally the same construction as discussed with regards to the standard coil winding 20 above. The efficient coil winding has first wires 31 with current traveling through them in a first direction and second wires 32 with current traveling through them in a second direction, opposite to the first direction. The wires 31 and 32 forming the coils are connected to input 34 and return lines 36 respectively, typically by crossing wires 33 and 35 respectively. The design of the coil wires 31 and 32 lead to increased efficiencies over the standard coil winding 20. Additionally, the crossing wire design can lead to increased efficiencies, together with or in place of the coil wires design. These advantages will be discussed in more detail below. While the majority of figures show an efficient coil winding design as discussed with respect to FIG. 3, the present invention can be applied to any coil winding design.

Figure 4:
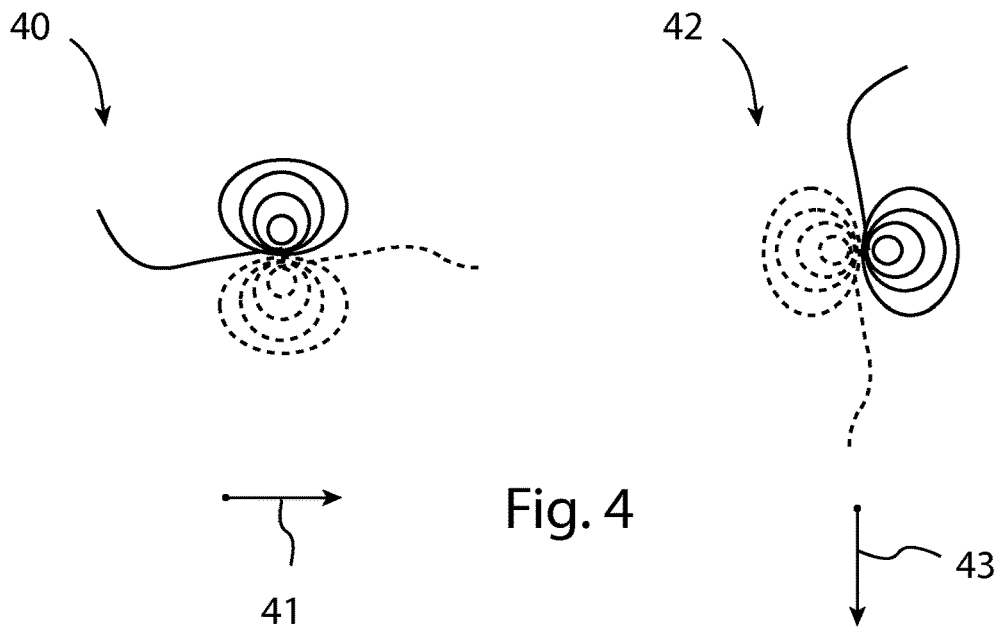
FIG. 4 shows two separate FIG. 8 coil windings and the predetermined direction of their intended magnetic fields.
Figure 5:
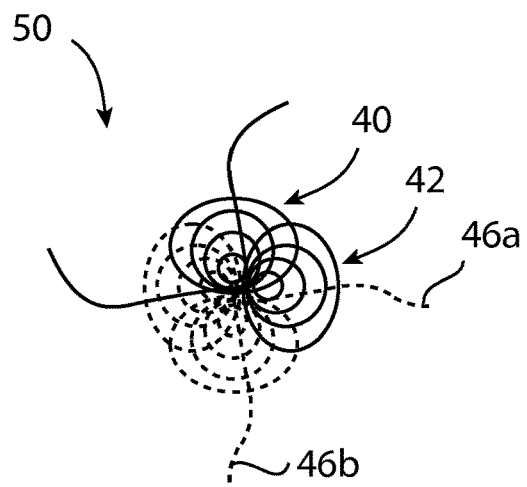
FIG. 5 shows the coil windings of FIG. 4 in an overlapping configuration oriented with an angle between them of 90 degrees.
Figure 5:
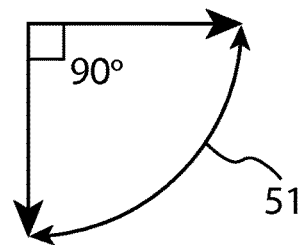

FIGS. 4 and 5 show a simple example of the present invention. FIG. 4 shows a first coil winding 40 and a second coil winding 42. The first and second coil windings are both shown with respective power input lines and returns. The direction of the electric field induced by the magnetic field to be generated by coil winding 40 is shown as 41. Similarly, the direction of the electric field induced by the magnetic field to be generated by coil winding 42 is shown as 43. In FIG. 4, the first and second coil windings are oriented 90 degrees to each other. Similarly, the directions of the electric fields to be generated are perpendicular to each other.

The direction 41 of the electric field induced by the magnetic field to be generated by coil winding 40 is an example of typical current technology in TMS coil devices where the direction of the current traveling through the coil cannot be freely chosen during operation. In other words, the current waveform in a typical system has the same polarity from one pulse to another, although the current waveform amplitude can be changed. However, in an example where the circuitry of the TMS device allows the direction of the current in a coil to be reversed then the direction of the resulting electric field could also extend up to 180 degrees from that currently shown. Additionally, these are some of the most basic, FIG. 8 coil winding examples with a straight forward generated magnetic field and induced electric field. Other coil winding designs produce different types and orientations of induced electric fields, some of which will be described below.

Each of the coil windings discussed herein is for generating a magnetic field and an induced electric field when a current is passed through them. Additionally, while numerous examples of coil geometries are discussed herein, within the mTMS coil device, the geometry of each coil will remain essentially the same, though some deformation may occur during use. Thus, each coil winding is for generating an electric field in at least one predetermined direction and orientation when a current is passed through the coil. As stated above, a coil winding may be for generating more than one electric field with a unique predetermined direction and/or orientation. For example as discussed above, wherein when a current is reversed in a coil the resultant electric field will differ, in a predetermined way, from the original electric field.

FIG. 5 shows the first coil winding 40 partially overlapping the second coil winding 42. The combination 50 of the two coil windings 40 and 42, in the orientation with respect to each other as shown in FIG. 4, results in the range of electric field generations as shown by 51, depending on the relative amplitudes of the currents in coil windings 40 and 42. Additionally, the return lines of each of the coil windings 40 and 42 are shown as 46a and 46b respectively.

By partially overlapping the two coil windings 40 and 42 it is possible to generate two individual electric fields, one from each coil winding, which then create a desired resultant electric field. By separately controlling each of the coil windings it is possible to have a virtually continuous range of resultant electric fields between the predetermined directions and orientations of each of the involved coil windings. With the example of coil windings 40 and 42, without the possibility of reversing the current direction through the coils windings, the resultant range 51 is 90 degrees, when the coils are arranged with 90 degrees between them.

Figure 6:
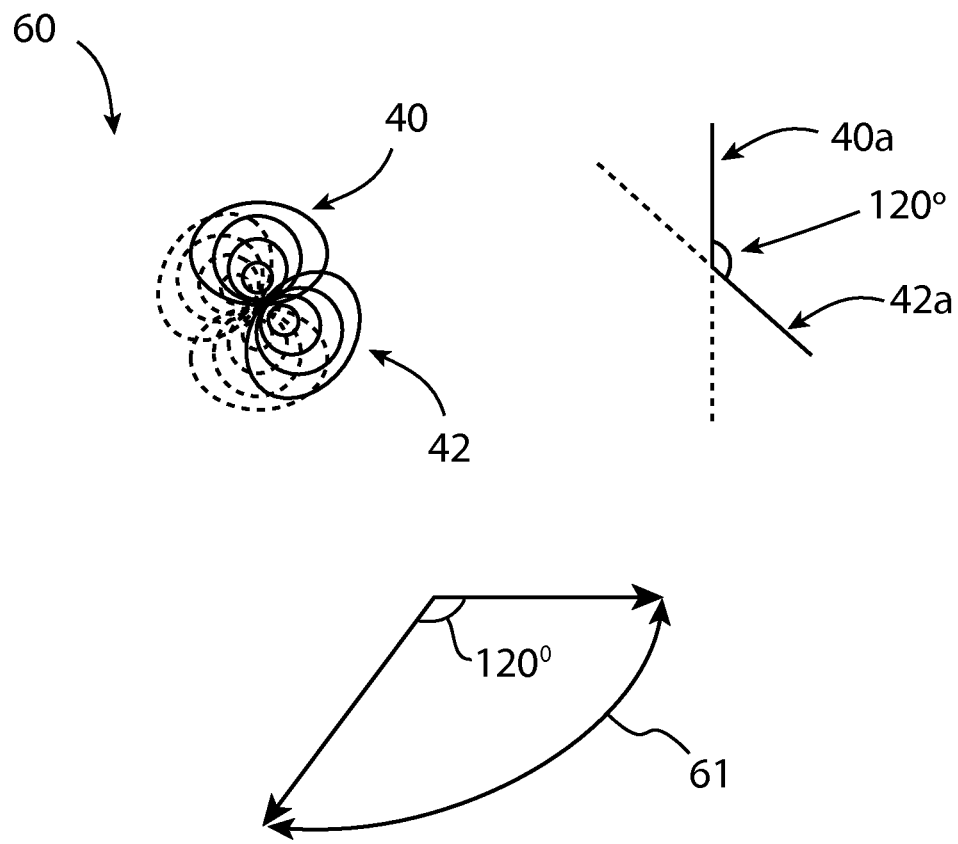
FIG. 6 shows the coil windings of FIG. 4 in an overlapping configuration oriented with an angle between them of 120 degrees.

A similar example is shown in FIG. 6 with a different combination 60 of coil windings 40 and 42. In combination 60, coil winding 42 is rotated 120 degrees from coil winding 40 which results in a range of resultant electric fields of 120 degrees, as represented by 61.

Figure 7A:
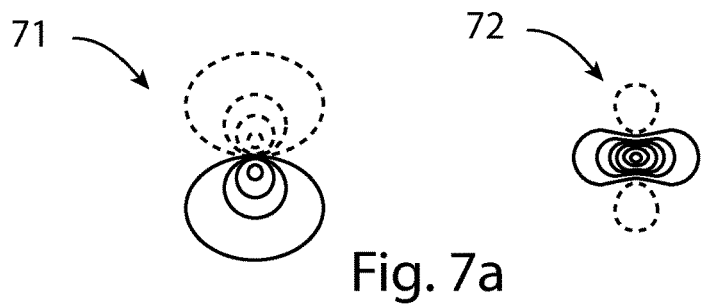
FIGS. 7a-7g show example combinations of unstacked coil windings.
Figure 7B:
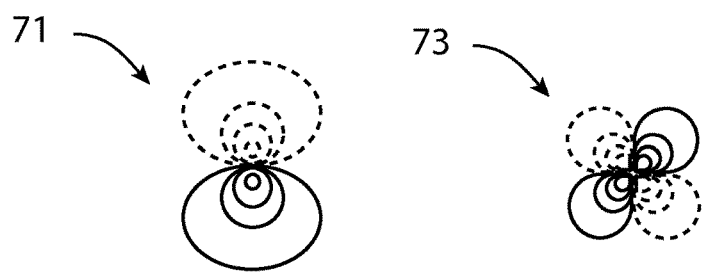
Figure 7C:
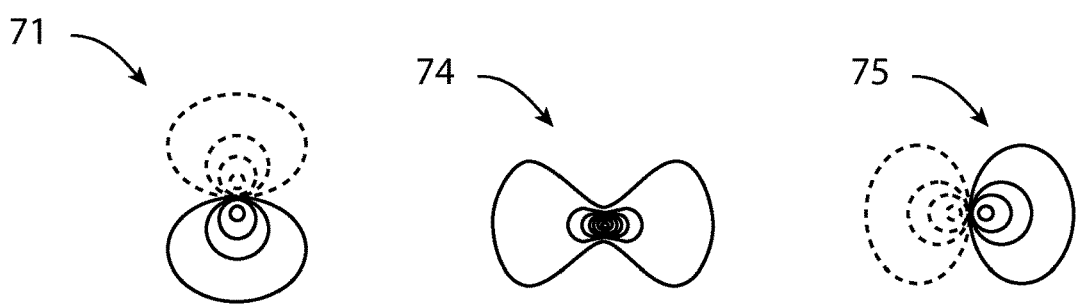
Figure 7D:
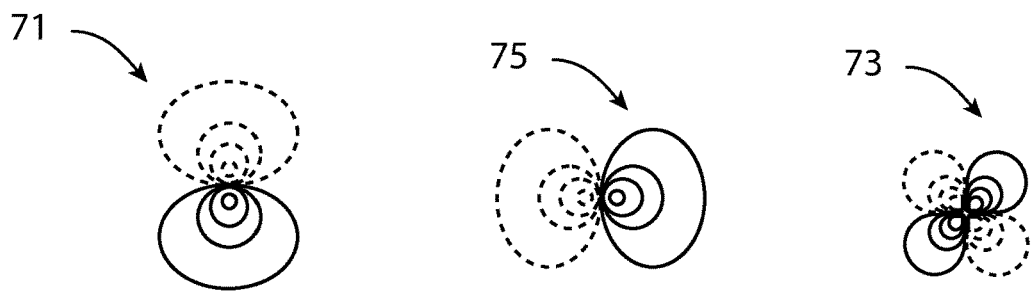
Figure 7E:
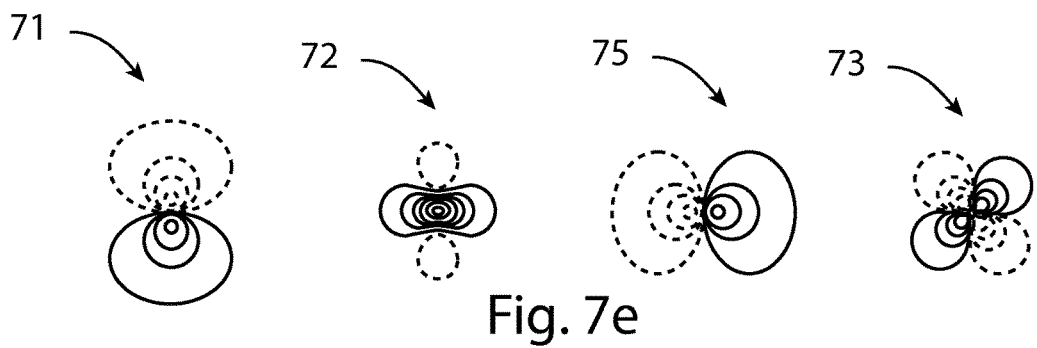
Figure 7F:
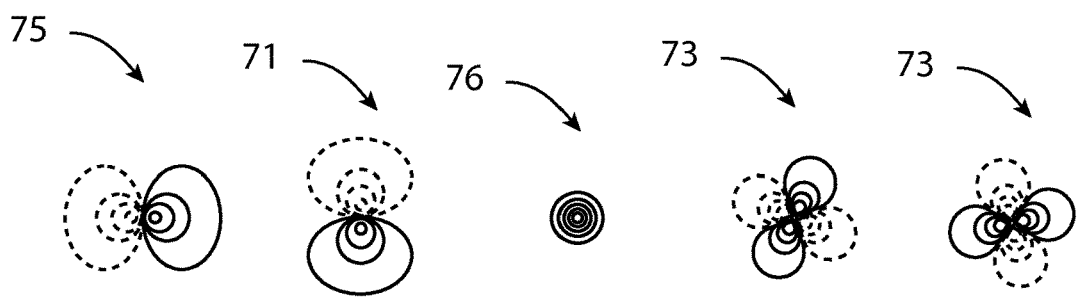
Figure 7G:
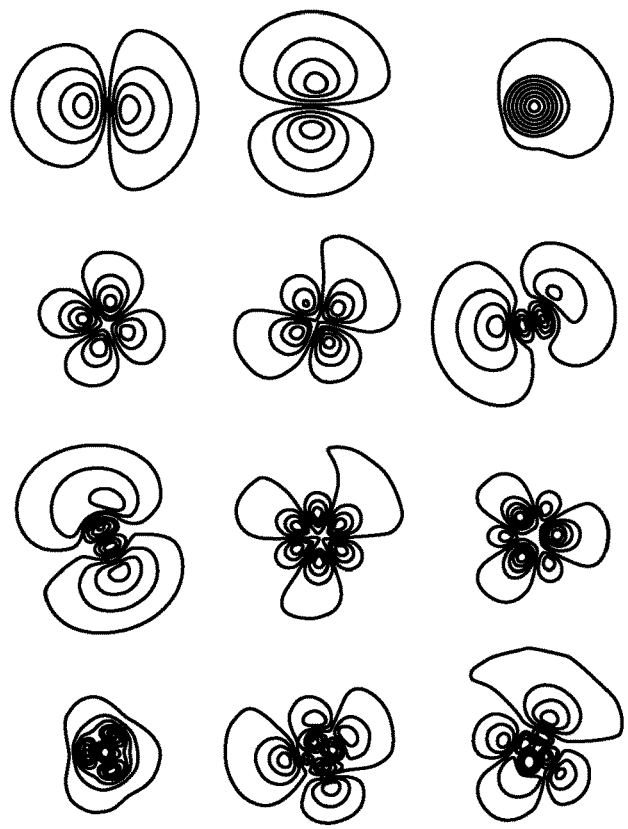
Figure 8:
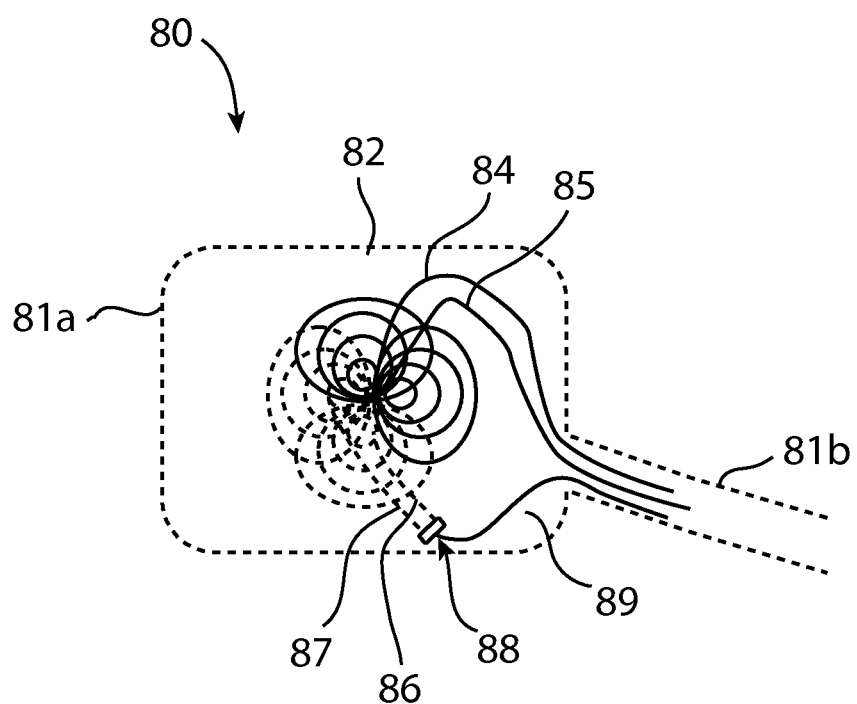
FIG. 8 shows an example of a pair of overlapped FIG. 8 coils in a single casing.

As shown in both FIGS. 5 and 6, each of the coil windings has essentially the same geometry, e.g. efficient FIG. 8 geometry, but are in different orientations. However, coil windings with different geometries can be used, as will be discussed with regards to at least FIG. 7 below.

As shown in the examples of FIGS. 5 and 6, each of the coils has an axis of symmetry and a center point. Coil windings typically have some axis of symmetry, as shown for example in FIGS. 7a-f. Additionally, all coil windings will have some center point, which could be a center of mass or a geometric center.

According to certain examples of the present invention, at least two, or each, of the coil windings will have an axis of symmetry and a center point. The overlapping combination of coils can be overlapped in numerous manners. One manner is that the center points of the coil windings are overlapping and then there is an angle between their respective axis's of symmetry. Another manner is with the center points of the coil windings offset from each other, e.g. wherein the center points are not overlapping.

Taking FIG. 5 as an example, when current is only passed through coil 40, the resultant electric field will be in direction 41. Similarly, when current is only passed through coil 42 the resultant electric field will be in direction 43. However, if current is passed through both coils simultaneously, the resultant electric field will be the sum of both individual electric fields and can be anything between directions 41 and 43. In an example where the current in each coil winding could be reversed during operation, then the resultant electric field could be generated anywhere within a 360 degree range.

While the coil windings can be the same geometry and same features, they may also be different, as shown in FIGS. 7a-g. Though not necessarily, the coil windings will be discussed herein as a primary coil winding and secondary coil windings. However, any of the coil windings could be equal to or subservient to others in operation regardless of their description herein.

As an example, a first coil winding 71 is a primary coil winding and is for generating a first, primary induced electric field. As a FIG. 8 coil is the standard coil in TMS coil devices, it is used herein as the first coil winding. However, any of the other coil windings could be considered the first coil winding. One or more additional, secondary, coil windings can then then be overlapped with the first and create secondary electric fields. The predetermined direction and/or orientation of the electric field to be generated by a secondary coil winding would thus typically be different from that of the first coil winding. Furthermore, secondary coil windings can be considered as for generating an electric field which is for altering some property of the first, primary electric field. For example, one or more secondary coil windings can be for altering, together or separately, the direction, position and/or orientation of the electric field of the first coil winding. Similarly, while the coils are physically overlapping they are typically overlapping in at least a predetermined direction of a electric field to be generated by at least one of the coil windings.

However, as discussed in more detail below, examples of the present invention can include one or more identical coil windings fully overlapped with each other, though not shown in the figures. One potential use for this would be to control the pulses separately, either at different times and/or simultaneously, for different advantages.

The different types of coils which are overlapped, and the manner in which they are over lapped, determine the types of controls the combination has over the resultant electric field.

In FIGS. 7a-g, the current is flowing counter-clockwise in the dashed wires and clockwise in black solid wires. These wires were computed for curved surfaces, and are projected into plane using azimuthal equidistant projection. The exact coil-winding shape can depend on a selected curvature, target depth, maximum coil size, and various other variables. This dependency is visible in the slightly varied shapes for the first order derivatives in different sets. Here, this variation is due to the numerical algorithms used to generate the coils. Note that also the number of turns in the coils may be changed to produce coils with desired properties.

FIGS. 4-6 show what we call here $0^{th}$ order derivative coil windings 40 and 42. Combining these coil windings, as discussed, allows for the rotation of electric field.

FIG. 7a shows a $0^{th}$ order derivative coil winding 71 and a $1^{st}$ order derivative coil winding 72. Combining these coil windings allows for vertical adjustments of a target position of a resultant electric field.

FIG. 7b shows a $0^{th}$ order derivative coil winding 71 and a different $1^{st}$ order derivative coil winding 73. Combining these coil windings allows for horizontal adjustments of a target position of a resultant electric field.

FIG. 7c shows two $0^{th}$ order derivative coil windings 71 and 75, in different orientations sandwiching a $1^{st}$ order derivative coil winding 74. Combining these three coil windings allows for vertical adjustments of a target position and orientation correction of a resultant electric field.

FIG. 7d shows two $0^{th}$ order derivative coil windings 71 and 75, in different orientations with a $1^{st}$ order derivative coil winding 73. Combining these three coil windings allows for horizontal adjustment of a target position with orientation correction of the resultant electric field.

FIG. 7e shows two $0^{th}$ order derivative coil windings 71 and 75, in different orientations sandwiching a $1^{st}$ order derivative coil winding 72 and also with a $1^{st}$ order derivative coil winding 73. Combining these four coil windings allows for horizontal and vertical adjustment of a target position along with orientation correction of the resultant electric field.

FIG. 7f shows two $0^{th}$ order derivative coil windings 75 and 71, in different orientations with three $1^{st}$ order derivative coil windings, 76 and two 73's in different orientations. Combining these five coil windings allows for horizontal and vertical adjustment of a target position along with arbitrary orientations of the resultant electric field within the range of possible orientations depending on whether the current circuitry is able to reverse current waveform polarities or not.

FIG. 7g shows an example of a 12-coil orthogonal layer coverage coil array. The coil array can have large, thin overlapping coils. As can be seen from the figures, the individual coils do not all have an axis of symmetry, yet all have a center.

In all of the examples so far, the ideal method of overlapping of the coil windings is to arrange their center points so that they are substantially overlapping. FIG. 8 is an example of the combined coils 82 housed within the casing 81a of an mTMS coil device 80. The combined coils 82, similar to those shown in FIG. 5, each have an input line 84 and 85 and return lines 87 and 86. In the present example, the return lines 87 and 86 of the two cables are connected, via a connector 88, to a single return line 89. The single return line and input lines are housed in the cabling 81b of the mTMS coil device 80 of the present example. The single return will be described in more detail below.

As seen in the example of FIG. 8, the first and second coil windings only partially overlap within the casing 81a. Essentially, the coil windings are stacked with one coil winding on top of the other coil winding. Typically the coil windings will be electrically separated from each other. Portions of the coil windings though may be electrically connected, for example via the connector 88 connecting the return lines 87 and 86 of each of the coil windings of the combination 82.

In most cases, the position and orientation of secondary coils will be fixed with respect to the position and orientation of the first coil winding. For example, when used in navigated TMS stimulation, it is important to know the position and orientation of all of the coil windings in a coil device during stimulation in order to know the exact electric field being generated. However, the position and/or orientation of one or more of the coil can be adjusted with respect to another coil winding or several windings during operation. In such examples, it is important that either the position and orientation of each coil is known or is derivable. Being able to adjust the physical relationship between two or more coils during operation adds an additional degree of control to the overall control of the resultant electric field. Some examples of this as such will be described below.

Additionally, though it has been described that the combination of multiple coils generally involves aligning and overlapping the center points of the multiple coils, the center points may also be offset. When overlapping the center points, any center point can be chosen, e.g. center of symmetry or center of gravity.

In a combination with more than 2 coil windings, not all coil windings need overlap with all other coil windings. While all coil windings may overlap, one coil may overlap two separate coils which do not overlap each other. Additionally, further non-overlapping coils can be housed in the casing of the mTMS coil device which do not overlap any of the other coils.

While primary and secondary coils and electric fields have been described, in typical implementations one coil is not significantly stronger than other coils. In these typical implementations all of the coils are nearly equally important, though they may be simply referred to as primary or secondary.

Coil combinations are typically a combination, or an approximate combination, of low order spatial derivatives of a focal TMS-coil induced 2D/3D vector electric field at some point. For 2D, this can be, for example, any combination of the coil windings shown in FIGS. 7a-g or similar such 2D designs. The combination can be a linear combination, e.g. the sum and difference pairs of the component coil windings. The combination can also be a non-linear combination, e.g. one half coil from one coil winding and another half coil from another coil winding. The combination can also be constructed from coil windings that are not derived as spatial derivatives of basic coil forms.

The coil windings of a combination may be orthogonal with respect to one or more of the other coil windings. However, non-orthogonal combinations of the coils are also possible. Orthogonality can result in zero mutual inductance. Additionally, orthogonality can result in the lead fields of the coil winding as being orthogonal in the space of the induced current patterns.

The efficiency of the coil windings can be effected by the shape of the wires of the coil winding as well as the wire dimensions. In addition to TMS, there are other uses for coil combinations. For uses such as magnetoencephalography (MEG), a thin wire, e.g. having a diameter on the order of 0.1 mm or less, can be ideal. For uses such as TMS, the wire diameter should be sufficient to accommodate high currents. However, thick wires may require larger currents, due to increased distance to a desired target and decreased number of loops. Therefore, the diameter of the coil winding can be selected based on the intended use of the coil device.

Additionally, the dimensions of the wire of the coil winding may be varied along the path of the coil winding. Thus, for example, thinner crossing wires, or even flattened wire, can be used in certain sections. Thus, a thinner coil and/or more stackable coil winding can be created.

The cross-sectional area of the coil windings can be varied, e.g. having smaller wire in certain parts. Furthermore, a non-circular filament can be used, e.g. where the crossing wire is twisted by 90 degrees. Such use allows for more coil loops while keeping the crossing thickness smaller than a circular filament.

As discussed herein, a wire means any material which has a non-zero conductance. Additionally, a wire can be used to form conducting paths isolated from the surroundings. The material can be high or low Tc superconducting or normal conducting material.

The mTMS coil devices described herein can be used for stimulating a target location on or within the brain of a subject. Stimulation electronics may include IGBT transistors, MOSFETs, thyristors or other suitable components. The polarity of the stimulation current waveform may be fixed or it may be controllable. If controllable it may be controllable with relays or transistors, for example. An example of a circuit design allowing polarity switching is described in FIG. 9 of U.S. Provisional application 61/830,181 filed Jun. 3, 2010 which is incorporated herein in its' entirety.

The number of channels in the stimulating electronics may be equal to or less than the number of coils in the mTMS device. Each coil may have its own electronics and capacitor(s). If there are less electronics channels than coils, the electronics may be connected to those coils which are needed for delivering a given stimulus at a given time. The connections to desired coils can be changed either manually or electronically, e.g. with switches.

The electronics may include a controller which controls the overall flow of current to the combination of coils in the mTMS coil device. One controller can be present for separately controlling the current in each of the coil windings power input line. Additionally, at least one controller can control the current in at least two coil windings power input lines.

Additionally, according to certain embodiments of the present invention, there is a method of controlling an mTMS coil in accordance with any of the embodiments and examples disclosed herein.

An mTMS coil can be controlled by controlling a first current through a power line of a first coil winding to generate a first electric field. As discussed above, for the purposes of the discussion, the first electric field can be considered a primary electric field.

Additionally, the position, direction and/or orientation of the primary electric field can be modified by separately controlling at least one second current through at least one second power line to generate at least one secondary magnetic field inducing at least one secondary electric field.

The position, direction and/or orientation of the primary electric field can also be modified by adjusting the position and/or orientation of the second coil winding with respect to the first coil winding.

The present methods can include the control of multiple coil windings, as show for example in FIGS. 7a-g.

Furthermore, the method can include the step of generating at least two magnetic pulses, with different target points and/or orientations. This can be done with the mTMS coil device in the same location and/or orientation. For example, with an mTMS coil device 80 of FIG. 8, by controlling the current in both FIG. 8 coils it is possible to fire multiple pulses from the same position and orientation of the casing but with the induced electric field from the resultant magnetic field being in different directions as discussed with respect to FIG. 5.

Additionally, the multiple, two or more, magnetic pulses can come within a short period of time, e.g. 200 microseconds to 2 seconds. The coil windings can be controlled such that at least two of the coil windings produce a magnetic field at the same time. Additionally, the coil windings can be controlled such that the at least two coil windings produce a magnetic field at the same frequency. Thus, the at least two coil windings will affect each other's induced electric fields on each pulse. By controlling the currents differently for different pulses, the induced electric fields can rapidly change without the need for physically moving the mTMS coil device.

Additionally, the at least two coil windings can be controlled such that the at least two coil windings produce a magnetic field at different frequencies. For example, one can produce pulses at a 10 Hz while another coil winding produces pulses at 5 Hz. Therefore, some pulses may be overlapping while others are not. Furthermore, at least two coil windings can be controlled such that their pulses never, or rarely overlap. Such an example could be used for increasing the rate of pulses by staggering two fully or partially overlapped coils.

Further variations are possible. For example, some coil(s) of a combination may be controlled in a biphasic manner while other(s) in the combination are controlled in a monophasic manner. Some coil(s) could produce slow pulses compared to another coil(s) producing faster pulses. Two pulses can be generated which essentially oscillate, have different frequencies, resonant frequencies or differ in another manner.

The method can further include the step of determining a location and/or orientation of the mTMS coil device. Furthermore, the method can include the step of determining a desired location and orientation of a target for an induced electric field and/or generated magnetic field. These can be a typical step of navigated TMS. Then, by separately controlling the generation of magnetic fields from multiple coil winding it is possible to generate a desired magnetic field and/or induced electric field, with a desired orientation at the target site.

A method can also include the steps of selecting a new target location and/or orientation for a magnetic/electric field to be generated, and separately controlling the generation of magnetic fields from the first and second coil windings of the mTMS coil device to generate a desired magnetic/electric field for the new target without adjusting the location or orientation of the mTMS coil device.

Without the use of an mTMS coil device in accordance with the present invention, someone using a TMS device needs to align both the physical position and physical orientation of a TMS coil device to produce a desired stimulus. If the user moves during stimulation, has trouble stabilizing the TMS coil device in one position or otherwise has difficulty using the device then providing accurate and desired stimulation with a human operator can be quite challenging. Using the present device and method, depending on the coil winding combination, the user need only generally align the mTMS coil device near a desired location and the system can compensate for any improper alignment through control of the different coil windings.

The methods described here may also be carried out by a computer program product stored on a transitory or non-transitory computer readable medium.

Further embodiments also include a processor and/or computer. Examples of computers are, e.g. a traditional computer one or more of its variants, e.g., a mobile phone, a tablet, or a customized device. A computer program product and/or control electronics for controlling the stimulation target and parameters may also be included.

A stimulus target can be considered to be, e.g., a single stimulus location with a given stimulus orientation and width, a single stimulus location with a set of different stimuli (e.g., stimuli with different directions, strengths, durations, or widths), or it may consist of or comprise several spatially distinct locations which are stimulated. Different targets can be stimulated simultaneously, or with desired delays. Some of the targets can be stimulated simultaneously while some are stimulated separately. The stimulation sequence can be specified by the user or it may be computed algorithmically. Repetitive TMS is also included as an option within this framework.

When a target is to be stimulated, the computer program product may compute the coil windings currents and/or their waveforms needed for delivering the desired stimulus to the target. The computational procedure may be based on e.g., a spherical head model, boundary element method, or finite element method. This computation can be done essentially online before a given stimulus or the computation can be based on using a lookup table and using precomputed parameter values (with possible correction terms, e.g., if the current amplitudes/ waveforms needs to be scaled), this can be considered as offline computation.

The multi coil winding arrangement allows for changing the stimulus target (or the stimulus orientation) without moving (or rotating) the coil(s). The stimulation target(s) can be specified by the user using a computer program product, computer program parameter or by moving the coil to a desired position. This can allow changing the stimulation region/changing the stimulus orientation, if the mTMS coil has a limited range of targets that it can stimulate, e.g., if it can stimulate only to a certain direction.

The computer program product may include an anatomical image, such as, e.g. MRI, CT image, a photograph, or a CAD model, of a subject's head/brain, on which a user may mark a desired stimulus target. Therefore the computer program product can know which targets the user wants to be stimulated. The computer program product may also keep track of the targets that have been stimulated.

Electronic targeting may take into account the coil or head movement. This may be based on measuring the respective position of the head and the coil. Thus, when the coil and head move with respect to each other, the computer program product adjusts the stimulus parameters accordingly, so that the desired stimulus e.g., a given electric field strength, is delivered to the target. This kind of adjustment can be performed also when the coil is adjusted to fit the subject's head, e.g., by deforming coils or positioning coil modules. If an mTMS coil, or one of a set of mTMS coils, has only partial coverage of a target region, the computer program product may assist the user for positioning the coil sufficiently close to the target so that a desired stimulus can be delivered to the target.

As mentioned above, the stimulus sequence may be based on a user-specified pattern or it may be designed algorithmically, for example using feedback from the system, e.g., measured electroencephalography (EEG) data or electric signals from the muscles. The mTMS device may be used together with EEG or other physiological measurement modality which can give feedback to the stimulation system. The feedback may be automatic (such as EEG data) or it may be given by an operator. The feedback may also be based on, e.g., the subjects/patients performance in a given task, e.g., object naming. The feedback data can be used to adjust/choose the parameters for the next stimulus (or some of the stimuli which occur later in time).

Furthermore, as mentioned above, a plurality of coil windings may share a single return line. For example, an mTMS coil device may comprise at least two coil windings in a casing. Each coil winding can have a power input line. The power input line of each coil winding may be separate or it may be shared among two or more coil windings. Furthermore, the at least two coil windings have a single, shared power return line.

In an mTMS coil device with several coil windings, some may have their own return lines and some may share a common return line. FIG. 8 shows an example of an mTMS coil device having a two coil combination 82 and sharing a single power return cable 89.

Each of the coil windings can have a separate power return line, for example return lines 87 and 86 in FIG. 8 and wherein the multichannel TMS coil device further comprises at least one connector 88 connecting the separate power return lines 86 and 87 to a shared power return line 89.

Furthermore, as can be seen in FIG. 8, the power return lines 86 and 87 can be oriented near to and/or overlapping each other. The path of the power return lines can be arranged separately within the casing and/or their desired location can be designed into the coil windings themselves.

Described herein is a multichannel Transcranial Magnetic Stimulation (mTMS) coil device comprising; at least two coil windings in a casing, wherein each coil winding has a power input line, and wherein at least two coil windings have a single, shared power return line. The mTMS coil device may also have all coil windings share the same shared power return. The mTMS coil device may also have a single power return. The mTMS coil device may also be such that each of the coil windings has a separate power return line, and wherein the multichannel TMS coil device further comprises at least one connector connecting the separate power return lines to the shared power return line. The mTMS coil device may also have the power return lines of at least two of the coil windings are oriented near to or overlapping each other. The mTMS coil device may also further comprise a casing which contains the at least two coil windings. The mTMS coil device may also have the casing including one power input cable per coil winding and at least one less power return cable than power input cables. The mTMS coil device may also have the power input cables of at least two of the coil windings separated from each other. The mTMS coil device may also have the coil windings stacked on top of each other. The mTMS coil device may also have at least two of the coil windings with substantially different geometries.

Furthermore, in magnetic stimulation and in related technologies, efficient coils are typically large. The basic reason is that the magnetic moment of a single-turn coil, if the current is fixed, is proportional to the square of its diameter, while the resistance is only linearly proportional to the diameter (with fixed wire diameter); the inductance is also proportional to the diameter (if the wire diameter is scaled in the same manner). Thus, a given pulse can be given with using smaller energies and currents in coils if the coils are larger. However, if a multiple-coil array is constructed, a problem may arises because in standard designs coils are made smaller if their density (number per unit area) is increased. Thus, the efficiency of the coils in typical multi-coil designs is sacrificed. In addition, the ability of small separate coils to produce a desired induced current in the target volume can be deficient.

Coils are usually made of wire that can not sufficiently support itself in the desired form. For this reason and to help build coils in the intended forms, coil formers are used. In the following, coil formers and coils are used sometimes interchangeably since coil formers define the shapes of the wiring of the coils.

The coil former may be either flat (i.e., a planar design) similar to the existing TMS coils, or curved (e.g., a spherical cap; the coil may also be bent at some points, e.g., at its edges) which may offer better coupling with the cerebral cortex. Especially in case of a curved coil former, the coil former may be made flexible, such that it can fit closer to the head. This flexibility can be obtained, e.g., by using a flexible coil-former material, such as rubber, or adding hinges into a rigid coil former. For the flexible material, fibers, such as glass fiber, can be used to obtain a flexible but non-stretchable coil former. This is because the Lorentz forces are usually oriented nearly tangentially with respect to the (local) coil-former orientation.

Larger coverage (of e.g., area/volume) for a coil array can be achieved in two general ways: using larger coil-former modules or combining several modules together. When several modules are connected, some of them can be selected to accommodate different head sizes. That is, there are a few variants of some modules allowing for TMS-helmet (or any other coil array) size adjustment. The coil-former connections may be made flexible to further enhance the fit. Also in case of a single-module mTMS instrument, there may be a variety of modules to fit different head sizes/shapes.

The change in the coil system may be automatic, e.g., motorized, or it may require the user to adjust it manually. The individual coil-former modules may partially overlap or cross neighboring modules. This can be used to ensure a seamless stimulus-position control over the module boundaries. The helmet, or in general any instrument holding the coil modules, which may not resemble a helmet, may comprise modules without coils, if some part of the head does not need to be covered.

Figure 9:
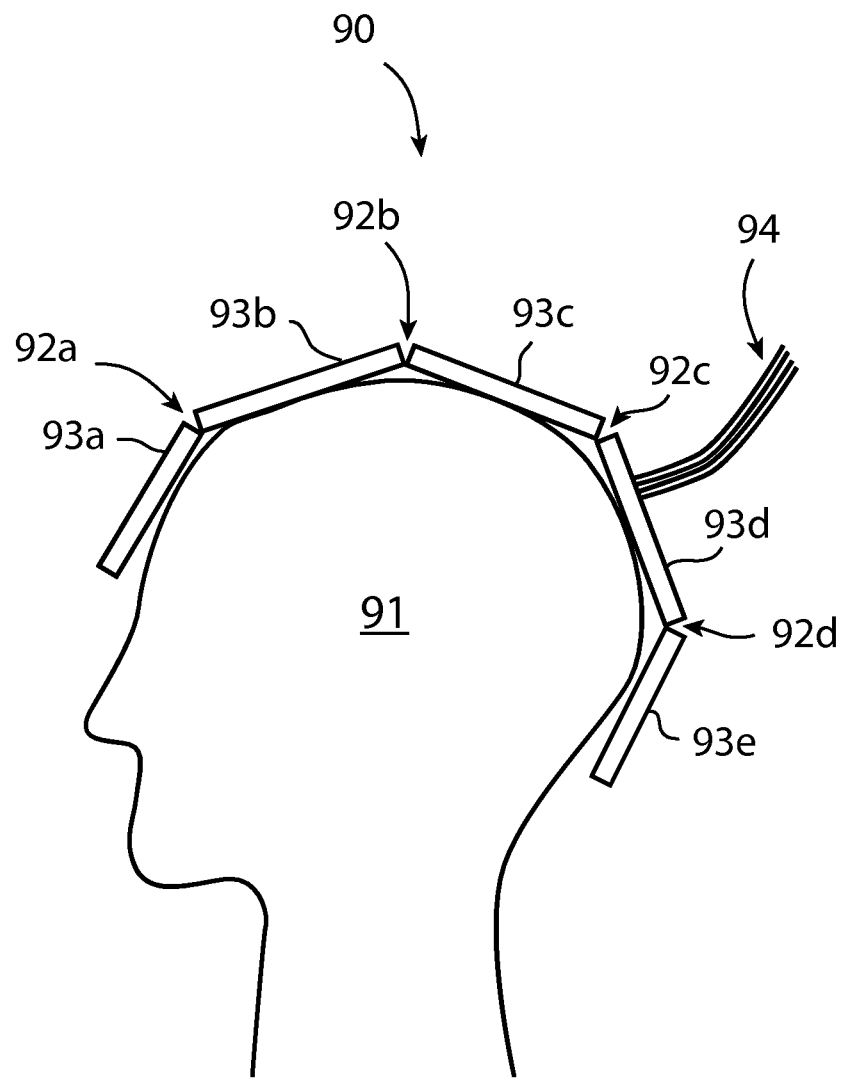
FIG. 9 shows a modular coil-former design with hinges between the modules and with non-overlapping modules.
Figure 10:
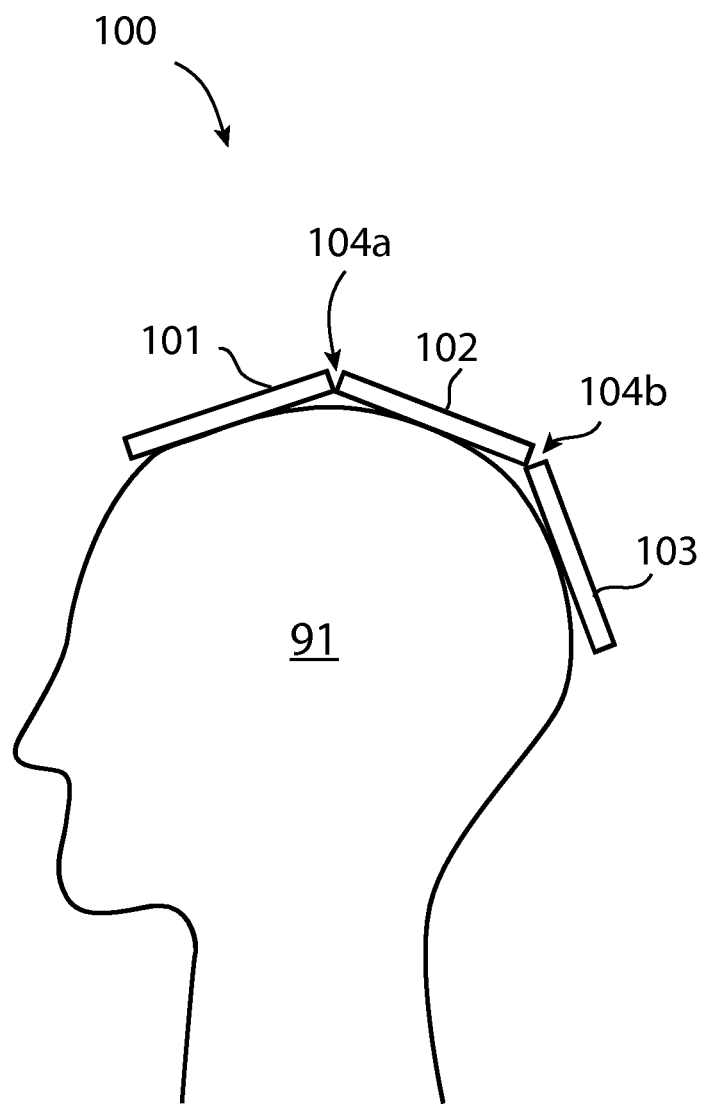
FIG. 10 shows a modular coil-former design with different sized and shaped modules.
Figure 11:
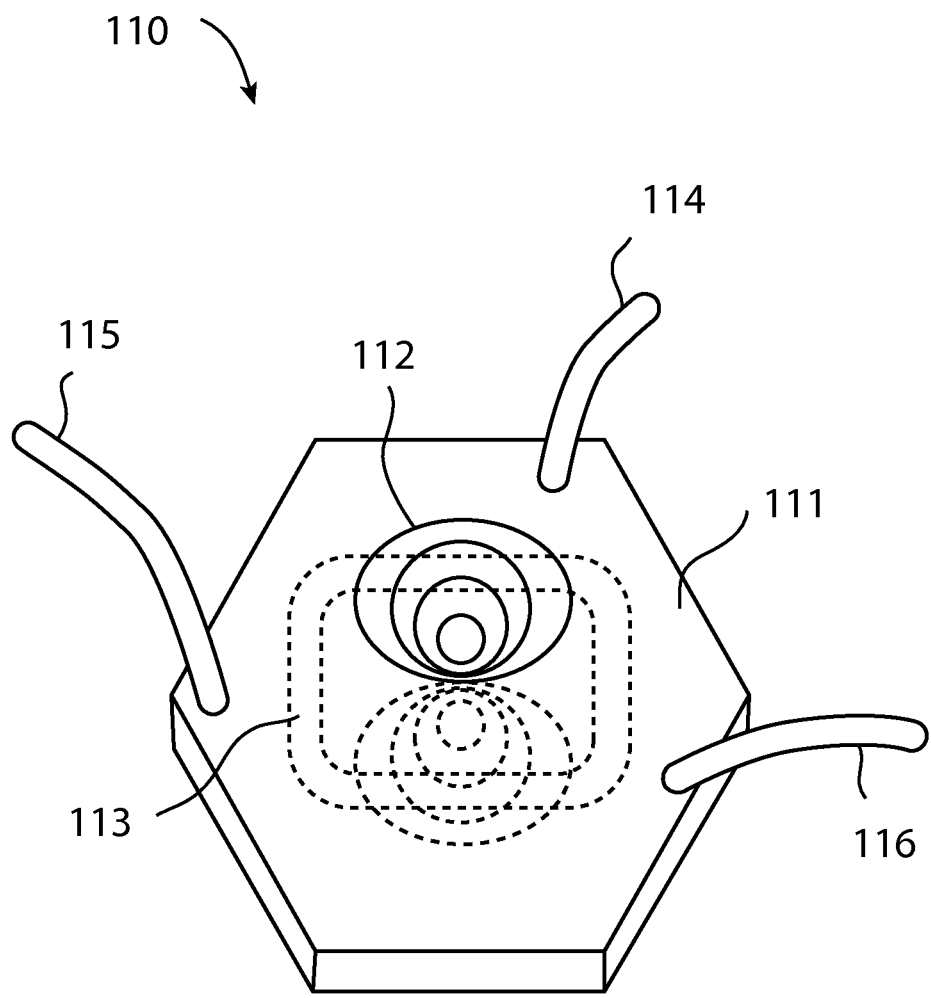
FIG. 11 shows an example hexagonal coil-former module containing overlapping coil windings.

FIGS. 9-11 show example helmet configurations. FIG. 9 shows a modular coil former design with hinges between the modules. Helmet 90 has 5 coil former modules 93a-e connected to each other by hinges 92a-d respectively. Due in part to the hinges, the helmet 90 can fit well on different sized heads 91. The helmet is shown with a single set of input/return cables 94. In the configuration as shown all of the coil former parts are rigid. However, not all coil former modules need to be the same nor all rigid.

FIG. 10 shows an example of another helmet 100 having three coil former modules 101-103 separated by hinges 104a and 104b. Helmet designs can have different coil former modules, for example module 103 could be curved to form the back of the head of a standard sized patient. To compensate for the larger and curved module 103, module 102 could be smaller.

FIG. 11 shows an example of a coil former module, in particular one of hexagonal shape. The coil former module can be an mTMS coil device as discussed above. A coil former module can also be the equivalent of a standard, single coil TMS coil device. However, the example of FIG. 11 is an mTMS coil device having a first FIG. 8 coil winding 112 and a second, ovular coil winding 113. In order to reduce the bulkiness of a single large input/return cable, the coil former module can have an input cable 114 for coil winding 112, a separate input cable 115 for coil winding 113 and a single, shared return cable 116 for both coil windings 112 and 113. Both coil windings being housed within the casing 111 of the module 110. However, the coil former module may have only a single power input/return cable and may be separate return lines for each of the coil windings housed therein. Similarly, the coil former module may have multiple additional coil windings as discussed above.

Next, we describe another approach for a whole-head stimulator or a stimulator having a wide stimulation area. The current patterns generated by the coils comprise N basis functions used to express the current vector field. For example, coils may be designed to approximate or be generated from representations of the real vector spherical harmonic basis functions (or their approximation). Components may be selected in their order of importance for the system (i.e., select all components that have an order less than given value). This basis can be computed to only cover the desired region of interest (position and orientation).

In case of small position corrections, this approach gives approximately the coils mentioned above. In case of larger coverage, the basis can also comprise oscillatory components. In case of almost whole head coverage, the (orthogonal) basis may have only oscillatory components. A linear (or some other) combination of the basis may be performed prior to forming the coils.

Figure 12:
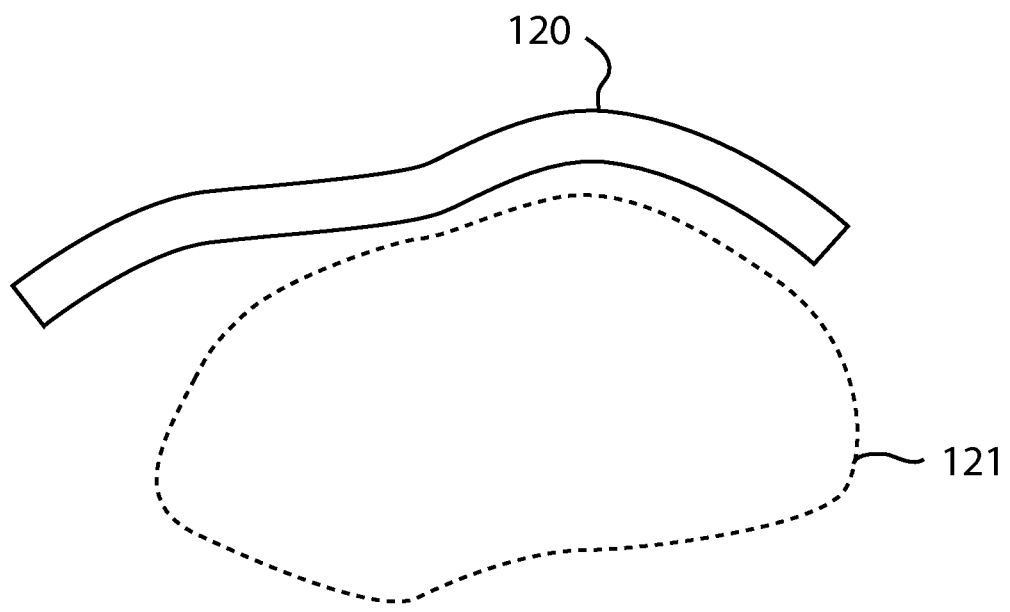
FIG. 12 shows an example coil-former module having a non-uniform shape.

The coil former may also be curved. If curved, it may have uniform or non-uniform curvature. It can be flat or even be non-convex. FIG. 12 shows an example of a non-uniform curvature to a coil former module 120. The shape of the coil former module 120 can be selected to mimic a specific target sight or tissue area 121.

Coil-former layers can be made thin. Because the coils may have crossing wires, the thinnest designs are non-trivial. A thin design can be achieved with various methods. Some non-trivial methods are described in FIGS. 13a-d.

Figure 13A:
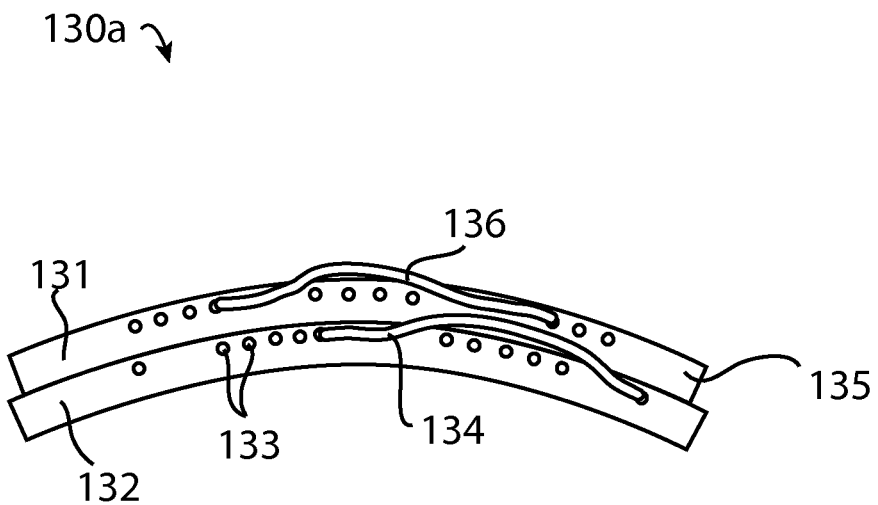
FIGS. 13a-d show examples of crossing wires for coil-former designs.

FIG. 13a shows a crossing wire example 130a with a $1^{st}$ coil winding 131 having a first crossing wire 136 and a $2^{nd}$ coil winding 132 with a second crossing wire 134. The second crossing wire 134 goes through the material 135 of the $1^{st}$ coil winding layer. FIG. 13a is a cross sectional view and shows the ends of the wires 133 forming the coil winding.

Figure 13B:
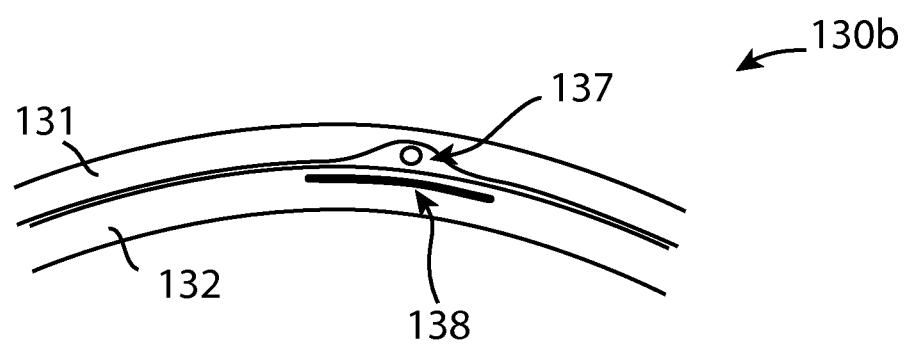

FIG. 13b shows a crossing wire example 130b where the $1^{st}$ coil winding 131 is deformed 3-dimensionaly around the crossing wire 137. 138 shows one of the wires making up the $2^{nd}$ coil winding 132.

Figure 13C:
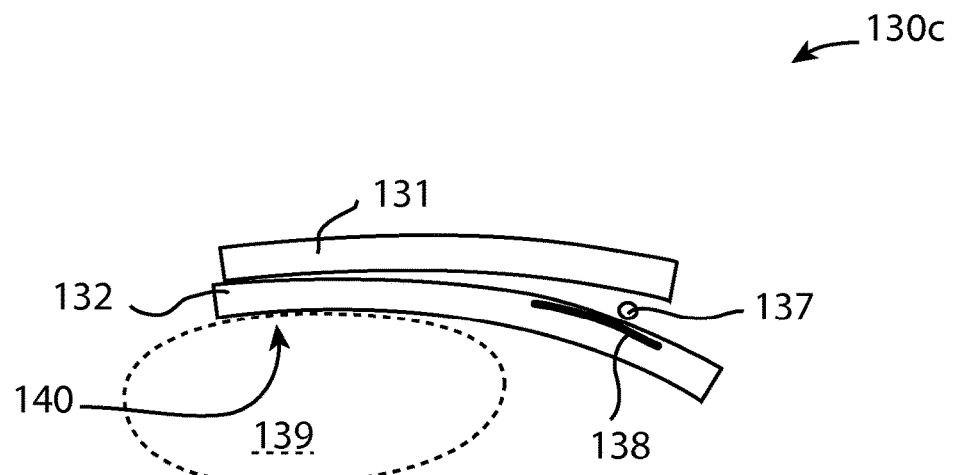

FIG. 13c shows a crossing wire example 130c where the crossing wire 137 is located farther from a target sport 140 in a tissue area 139.

Figure 13D:
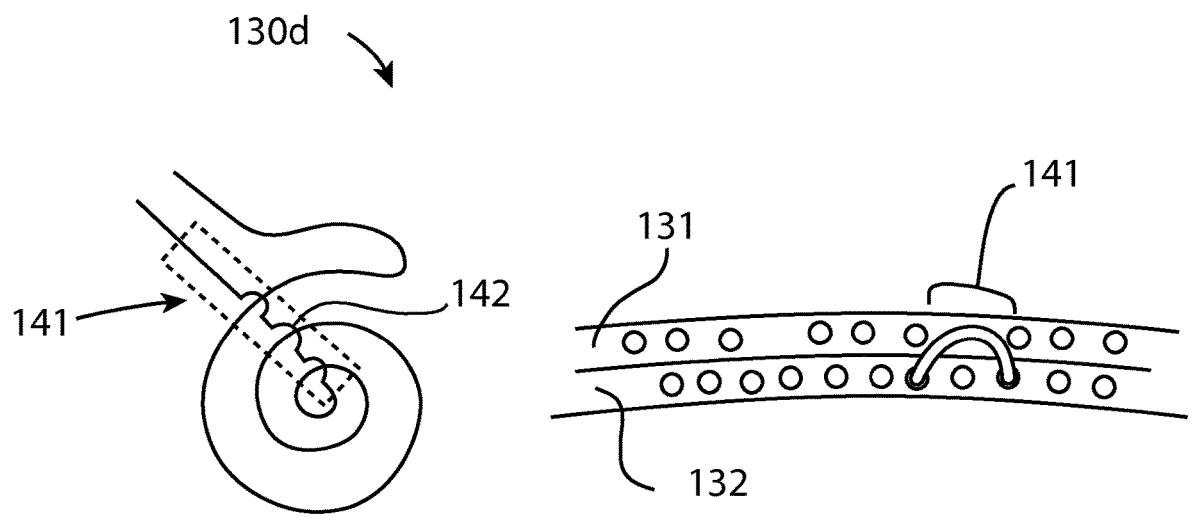

FIG. 13d shows a crossing wire example 130d where a next coil winding is designed such that it does not overlay with the crossing wire of an earlier coil winding. In particular, the $1^{st}$ coil winding is designed to not have wires 133 in the area 141 including the crossing wire 142 of the $2^{nd}$ coil winding 132.

Positioning the crossing wires into the structural part of the coil former for the next coil removes any unnecessary thickness from the coil former. Optimizing the positions of crossing wires can be so that crossing wires may be located farther from the target region, where the coil-former thickness is not equally important. For example, the individual coil loops may be connected outside the region of interest. Ensuring that the crossing wires do not interfere with the next coil layer, for example position them away from the densest wiring can be helpful as well.

Optimizing the next coil based on the previous coil crossing wires can include that the design for the next coil may disallow a wire that would cross the crossing wire from the previous coil. This allows for removing the crossing-wire layers entirely. It is also possible to make two (or more) coils share a layer for the crossing wires. This removes every other crossing wires layer.

This sharing may also be partial when the layer sharing occurs, say, only in the densest region of wires. In, say, more distant locations the coils may have their own layers where they cross. A crossing layer may also be (at least partially) shared by coils having at least one other coil between them.

The wire connecting the said coil turns/loops may be (at least partly) essentially perpendicular to the coils so that the connecting wire may penetrate through several coil layers when passing other coils. Superconducting wire/leads may be used instead of normal conducting material.

The described coil designs are suitable for magnetic stimulating modalities, such as transcranial magnetic stimulation (TMS); biomagnetic measurements, such as magnetoencephalography (MEG) and magnetocardiography (MCG); nuclear magnetic resonance (NMR); magnetic relaxometry; magnetic impedance tomography; magnetic resonance imaging (MRI), including ultra-low-field (ULF) MRI, low-field MRI, and high-field MRI, both clinical and non-clinical MRI; microwave tomography, where microwave signals are transmitted to and received from a body under investigation; magnetic particle imaging; and similar/related technologies.

The properties (or design principles) of the coils/coil array described for mTMS may also be applied for all these modalities. In all these applications the coils may or may not be resonant circuits, similar to, e.g., B1 coils in high-field MRI. Note also that instead of head a similar coil array can be constructed for imaging/stimulating any other body part, or even nonhuman samples/targets. In any of the mentioned areas, the coils may or may not be placed inside a dewar holding, e.g, liquid nitrogen of liquid helium. The coils may also be cooled, e.g., by means of air flow, moving liquid, moving solid material, or using thermally conductive material in connection with or in the vicinity of the coils.

In biomagnetic applications, such as in MEG, which is reciprocal to TMS, a similar coil array will be useful. In these applications, the coils can be made of thin (superconducting, or normal conducting, e.g., copper) wire/leads further enhancing the optimality of the coupling to the target. In these applications, large thin overlapping coils may form a set of so-called pickup loops. These pickup loops can then be connected to measuring sensors (such as superconducting quantum interference devices, SQUIDs, atomic magnetometers, or sensors based on giant magnetoresistance, such as so-called mixed sensors).

Figure 14:
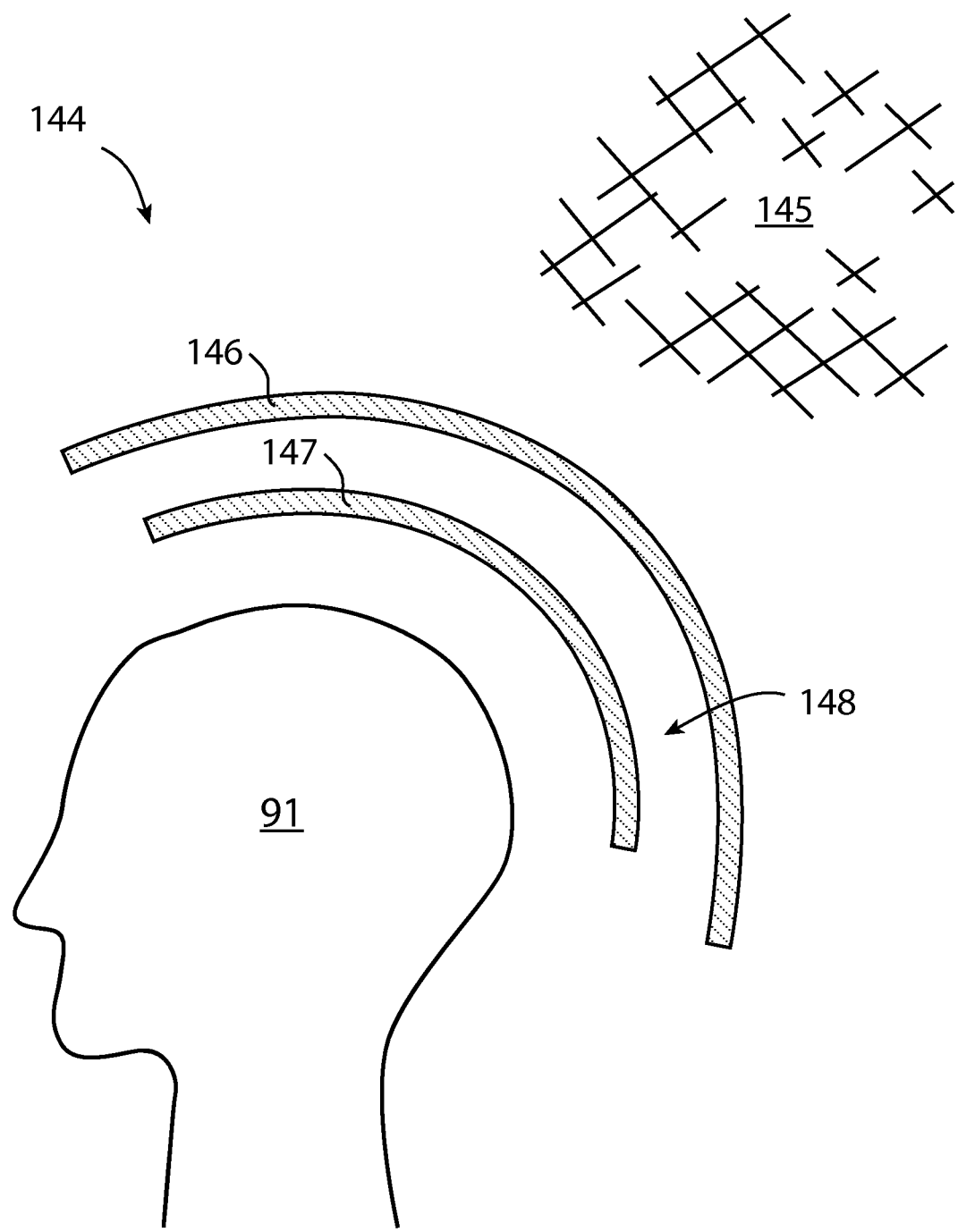
FIG. 14 shows an example of large overlapping coils for MEG.

A coil array may have a planar/cylindrical/spherical/related structure similar to the described TMS coils. Because in these applications it may be useful to have sensors also further away from the target, the coils may resemble gradiometric coils, e.g., if the coils are formed by connecting coils situated at two separate regions (such as coils on two concentric (e.g., spherical or nearly head-shaped) surfaces, or on two planar/cylindrical surfaces having different distances to the target). A figure of such an arrangement FIG. 14. FIG. 14 shows a layer of large thin overlapping coils 147 and another layer of large thin overlapping coils 146 above and separated by a gap 148 which form the device 144 and which is good. In these applications, the coils may have a form that reduces the interference signals sensed from the environment 145 or other location. These designs may result from solving an optimization problem similar to the mTMS design problem, but with different cost/utility function, which may take into account, e.g., sensor noise, system noise, or noise from the environment. The resulting array may comprise large overlapping orthogonal coils which may or may not resemble, e.g., discretized vector spherical harmonics.

In (ULF/LF/high-field) MRI, a similar multicoil design can be reached. In MRI, such an array can be used to transmit signals: they can be used to produce the so-called B1, spin-flip, or radio-frequency pulses by having suitable currents in the coils. The coil array may also be used to receive signals from the object/sample/body under investigation. However, in this case, the resulting coil geometry may differ from the mTMS coil array because the underlying sources of MRI signals are magnetic dipoles and not current dipoles, which form, e.g., MEG and MCG signals. Coil arrays comprising large overlapping coils for MRI applications may have practically zero mutual inductances between all pairs of coils (optionally a tuning mechanism may be included to further reduce their coupling). The coil array may also be designed to couple only weakly to specific kinds of noise sources.

A similar coil array comprising large thin overlapping coils can also be used in other applications where signals are both transmitted and received. One such technology is microwave tomography which may be used, e.g., for medical diagnostics. In these cases, the transmit-receiver coil (or antenna) array may be designed to have coils having (nearly/practically) zero mutual inductance between each other. This may enhance detecting weak targets as the transmitted signal is (mainly) only measured if there is a target. For example the coil array may have a design and calibration that produces nearly no signals when a healthy/undamaged subject/object is imaged/measured. However, in the presence of, say, bleeding within the tissue the coupling can change and a signal may be detected. In these applications the coil array may have a shape different from mTMS coils, as the microwave signals oscillate at high frequencies and they cannot be considered quasi-static. Although a different implementation of the design algorithm may thus be useful, the coil array may still have the same characteristic properties, e.g., orthogonality between the coils/channels.

In addition to the above-mentioned applications, a coil array having large thin overlapping coils may benefit certain other tasks. For example, one could consider studying the movement of, say, fish or other creatures in, say, an aquarium or under a boat. Then a coil/sensor array having a design similar to the one described in these documents outside the said aquarium or attached to the boat may reveal how the said fish or other creatures move or where they are located.

Although the above description only describes areas where the target to be measured/stimulated may be considered to be close to the coil array, an equivalent coil array may also be used in applications where said signals are received or transmitted from/to targets situated at distances larger than the characteristic coil dimensions from the coil array.

A hinge herein means, in addition to a hinge, any means to connect two or more said pieces in a way that allows the angle between the pieces to be changed. Coil winding stand means not only for a coil but also for other similar entities, e.g., antennas, or resonant circuits. A coil winding may also have various components/circuit elements in series/parallel.

The general advantage is better coupling with the tissue for individual coils (leading to enhanced signal-to-noise ratio (SNR) for imaging and smaller power requirements for stimulation). TMS can be made more efficient, i.e., the desired stimulating effect can be achieved with smaller currents than with old designs. Similarly, MEG can be measured with smaller instrumental noise than with previously known arrays. Likewise, MRI, NMR or other magnetic signals can be measured with smaller noise levels than with previously known solutions.

One TMS specific advantage is to have spatially overlapping lead fields, which allow more precise stimulus position control. This allows for precise electronic correction of the coil position and orientation in relation to the stimulation target (e.g., a specific location at the primary motor cortex).

Figure 15A:
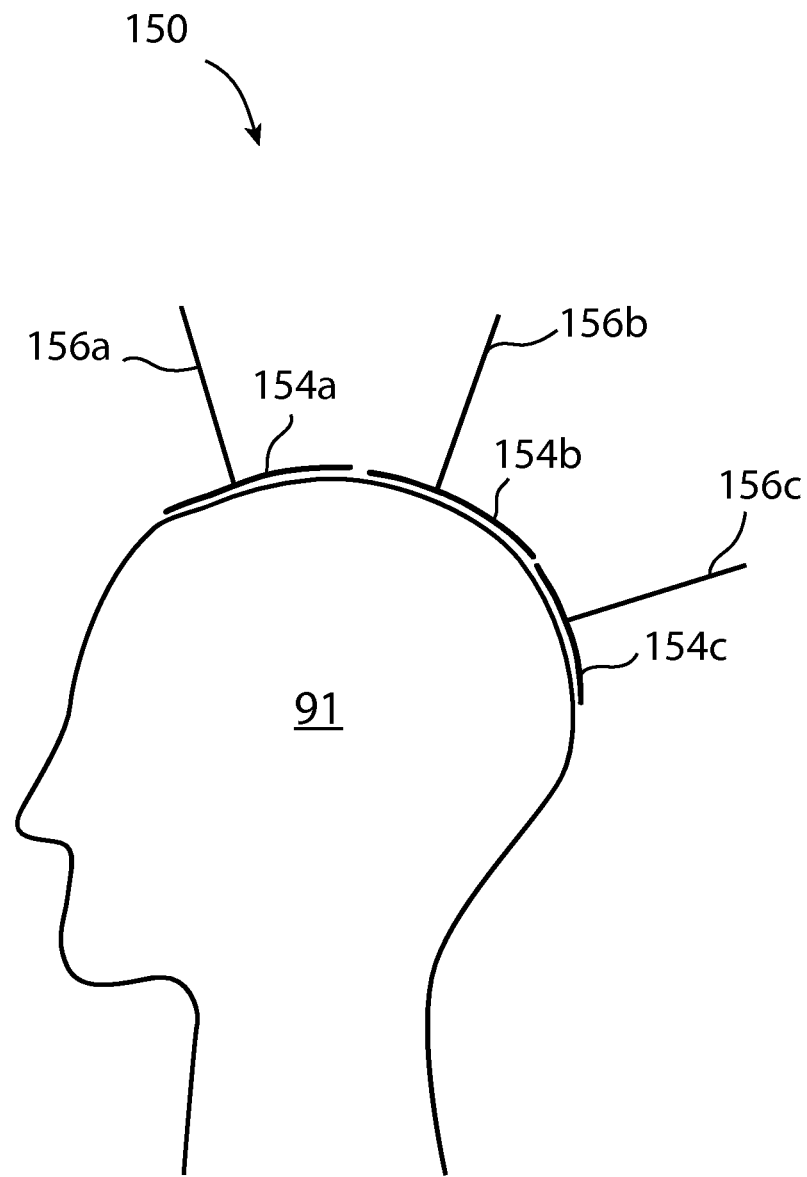
FIGS. 15a-b show examples of modular, non-connected coil systems.
Figure 15B:
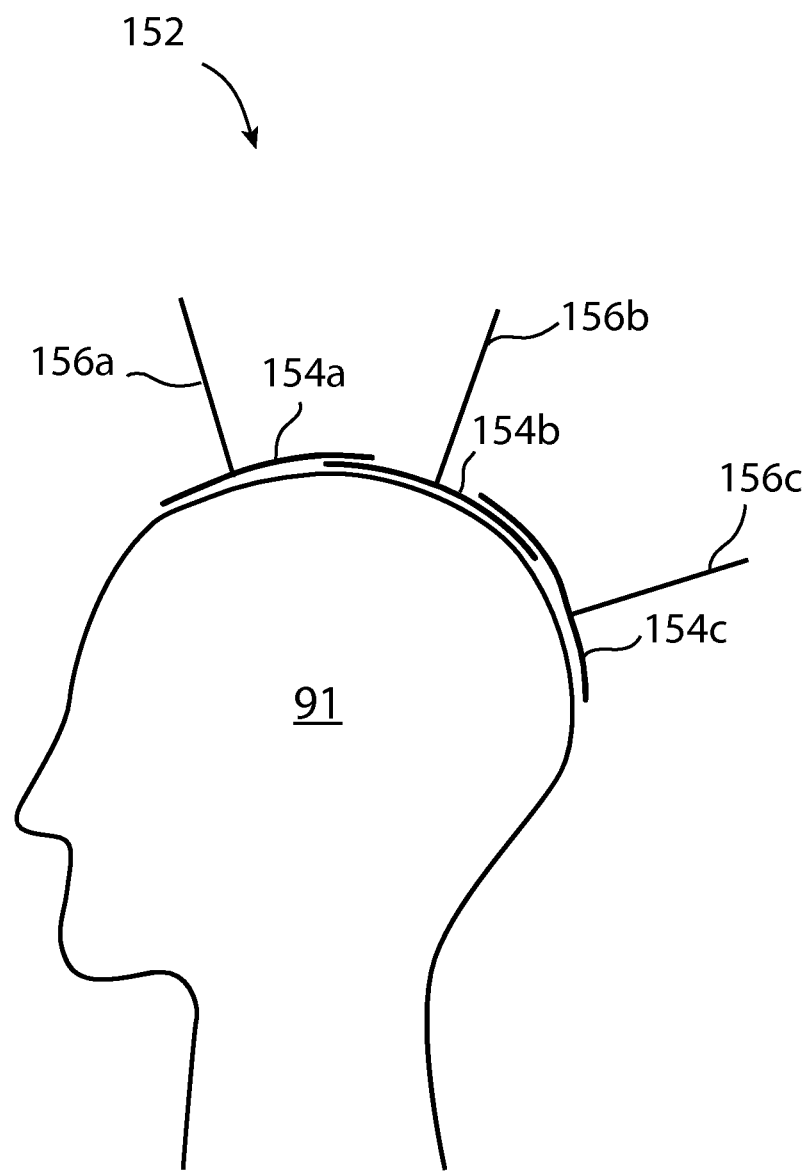

FIGS. 15a and b show examples of coil systems 150 and 152 respectively where the coil modules 154a-c are not connected to each other. Indeed, some or all of the coils may be placed at desired positions by using their own coil holders 156a-c (which may be thin or thick, have several or one said holder elements, the holder elements may be attached close to the center of the modules or elsewhere, etc.). This may also be considered as one implementation of a hinge. The coil modules (some or all of them) may partially or completely overlap each other. The said coil holders may also penetrate through (other) coil modules/holders. The said coil holders may extend to any desired direction from the subject (for example, they may be essentially radial (or perpendicular), as in the figures, or they may be more tangential). In this implementation, as well as in the other implementations, the coil modules may be kept in place, e.g., by a said user or they may be attached to some stand or an equivalent support. The said stand may be, e.g., standing on a floor, attached to a wall, or hanging from a ceiling. Also in all cases, the modules may or may not touch the subject/patient;

Furthermore, there may be a gap/gaps between the modules. According to yet another embodiment, the coil modules may form a wearable helmet that a subject/patient may carry without additional support. Such a helmet may allow the subject/patient to move more freely while he/she is stimulated (and/or measured). Different implementations of a coil array may be combined to form new implementations (e.g., in addition to a wearable helmet, some additional coils/or an extra coil may be provided via coil holder(s)). The coil modules may be constructed so that they, in a way, lock to each other (in addition to coils being completely above or below other modules, they may penetrate inside other modules and/or the modules may also have a structure which makes them stay together).

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A multichannel Transcranial Magnetic Stimulation (mTMS) coil device comprising:
   a rigid casing,
   a first coil winding housed within the rigid casing having a first power input line, and
   a second coil winding housed within the rigid casing having a second power input line, the second coil winding having a different geometry than the first coil winding,
   wherein the first and second coil windings each have a center point, and the first and second coil windings are affixed within the casing such that the center points of the first and second coils are overlapping.

2. The mTMS coil device according to claim 1, wherein the first and second coil windings are each for generating an induced electric field in at least one predetermined direction and orientation when a current is passed through the first and second coil windings.

3. The mTMS coil device according to claim 2, wherein the predetermined direction and orientation of the induced electric field to be generated by the second coil winding is different from that of the first coil winding.

4. The mTMS coil device according to claim 2, wherein the second coil winding is for generating an electric field for altering at least one of the direction, position and orientation of the electric field of the first coil winding.

5. The mTMS coil device according to claim 1, wherein the first and second coil windings each have an axis of symmetry, wherein the first and second coil are arranged with an angle between their respective axes of symmetry.

6. The mTMS coil device according to claim 1, wherein one of the coil windings is stacked on top of, but electrically separated from, the other coil winding.

7. The mTMS coil device according to claim 1, wherein the position and orientation of the second coil winding is fixed with respect to the first coil winding.

8. The mTMS coil device according to claim 1, having at least one additional coil winding.

9. The mTMS coil device according to claim 1, further comprising a controller for separately controlling a current in each of the coil windings' power input line.

10. The mTMS coil device according to claim 1, wherein the rigid casing comprises hinges between modules.

11. The mTMS coil device according to claim 1, wherein the coil device is configured to deliver TMS.

12. The mTMS coil device according to claim 1, wherein one of the coil windings is a FIG. 8 coil winding.

13. The mTMS coil device according to claim 1, wherein the center points overlap in a plane perpendicular to an axis of symmetry of one of the coil windings.

14. The mTMS coil device according to claim 1, wherein the center points overlap when viewed towards a direction of intended stimulation of at least one of the coil windings.

15. A method of controlling a multichannel Transcranial Magnetic Stimulation (mTMS) coil having at least two coil windings, comprising the steps of:
   determining a target location within the brain of an individual,
   controlling a first current through a first power line of a first coil winding to generate a first, primary electric field, and
   modifying the position, direction and/or orientation of the primary electric field by separately controlling a second current through a second power line of a second coil winding to generate a second, secondary electric field such that the modified primary electric field targets the target location within the brain of an individual, the second coil winding having a different geometry than the first coil winding,
   wherein the first and second coil windings each have a center point, and the first and second coils are arranged with their center points overlapping.

16. The method in accordance with claim 15, further comprising the step of generating at least two electromagnetic pulses with different target points and/or orientations with the mTMS coil device in the same location and orientation.

17. The method in accordance with claim 15, wherein one of the coil windings is a FIG. 8 coil winding.

18. A non-transitory computer readable medium having stored thereon a set of computer readable instructions for causing a processor to carry out the steps of:
   determining a target location within the brain of an individual,
   controlling a first current through a first power line of a first coil winding to generate a first, primary electric field, and
   modifying the position, strength, direction and/or orientation of the primary electric field by separately controlling a second current through a second power line of a second coil winding to generate a second, secondary electric field such that the modified primary electric field targets the target location within the brain of an individual, the second coil winding having a different geometry than the first coil winding,
   wherein the first and second coil windings each have a center point, and the center points of the first and second coil windings are overlapping.

* * * * *